US009267100B2

(12) United States Patent
Selker et al.

(10) Patent No.: US 9,267,100 B2
(45) Date of Patent: *Feb. 23, 2016

(54) COMPOSITE SENSOR ASSEMBLIES FOR SINGLE USE BIOREACTORS

(75) Inventors: Mark Selker, Los Altos Hills, CA (US); Timothy Johnston, Grass Valley, CA (US); Barbara Paldus, Woodside, CA (US)

(73) Assignee: Finesse Solutions, Inc., Santa Clara, CA (US)

( * ) Notice: Subject to any disclaimer, the term of this patent is extended or adjusted under 35 U.S.C. 154(b) by 701 days.

This patent is subject to a terminal disclaimer.

(21) Appl. No.: 13/385,100

(22) Filed: Feb. 2, 2012

(65) Prior Publication Data
US 2012/0244609 A1 Sep. 27, 2012

Related U.S. Application Data

(63) Continuation-in-part of application No. 13/134,157, filed on May 31, 2011, which is a continuation-in-part of application No. 11/728,560, filed on Mar. 26, 2007, now Pat. No. 8,008,065.

(60) Provisional application No. 60/835,329, filed on Aug. 2, 2006, provisional application No. 61/465,849, filed on Mar. 25, 2011.

(51) Int. Cl.
C12M 1/00 (2006.01)
G01N 21/359 (2014.01)
(Continued)

(52) U.S. Cl.
CPC ............ *C12M 23/00* (2013.01); *G01N 21/359* (2013.01); *G01N 21/552* (2013.01); *G01N 21/65* (2013.01); *G01N 21/8507* (2013.01)

(58) Field of Classification Search
USPC ............................................. 435/283.1–309.4
See application file for complete search history.

(56) References Cited

U.S. PATENT DOCUMENTS 4,163,903 A   8/1979   Robertson
4,353,488 A   10/1982  Schneiter et al.
(Continued)

FOREIGN PATENT DOCUMENTS

CN   101583866   11/2009
CN   101812405   8/2010
(Continued)

OTHER PUBLICATIONS

US Office Action dated Aug. 5, 2010 issued in U.S. Appl. No. 11/728,560.
(Continued)

Primary Examiner — Nathan Bowers
Assistant Examiner — Lydia Edwards
(74) Attorney, Agent, or Firm — Weaver Austin Villeneuve & Sampson LLP

(57) ABSTRACT

A composite sensor assembly for monitoring bio-processes which is suitable for use with a polymeric bioprocess vessel or with downstream equipment, and comprises:
i) a port comprising a high surface tension thermoplastic having a hollow tubular portion and a base plate portion, the base plate portion being fusibly sealable to the bioreactor vessel at a hole in the wall thereof;
ii) a generally opaque polymeric monitoring sensor assembly including electrical, and/or optical measurement components. The sensor assembly fits inside the bore of the hollow tubular portion of the port, and is adhesively retained therein.

19 Claims, 17 Drawing Sheets

(51) Int. Cl.
  *G01N 21/552* (2014.01)
  *G01N 21/65* (2006.01)
  *G01N 21/85* (2006.01)

(56) References Cited

U.S. PATENT DOCUMENTS

| | | | |
|---|---|---|---|
| 4,482,585 A * | 11/1984 | Ohodaira et al. | 428/35.2 |
| 6,190,913 B1 | 2/2001 | Singh | |
| 7,384,783 B2 | 6/2008 | Kunas et al. | |
| 7,434,448 B2 | 10/2008 | Weyl et al. | |
| 7,489,402 B2 | 2/2009 | Selker et al. | |
| 7,824,902 B2 | 11/2010 | Selker et al. | |
| 7,935,253 B2 | 5/2011 | Beulay et al. | |
| 8,008,065 B2 | 8/2011 | Selker et al. | |
| 2001/0015227 A1 | 8/2001 | Jorgensen et al. | |
| 2002/0038925 A1 | 4/2002 | Reimer | |
| 2002/0179444 A1 | 12/2002 | Lauks | |
| 2004/0058453 A1 | 3/2004 | Free et al. | |
| 2005/0239198 A1 | 10/2005 | Kunas et al. | |
| 2005/0239199 A1 | 10/2005 | Kunas et al. | |
| 2005/0272146 A1 | 12/2005 | Hodge et al. | |
| 2006/0240456 A1 | 10/2006 | Chen et al. | |
| 2007/0056353 A1 | 3/2007 | Weyl et al. | |
| 2007/0157748 A1 | 7/2007 | Baumfalk et al. | |
| 2008/0032389 A1 * | 2/2008 | Selker et al. | 435/283.1 |
| 2008/0171383 A1 * | 7/2008 | Selker et al. | 435/288.7 |
| 2011/0113900 A1 | 5/2011 | Goodwin | |
| 2011/0187388 A1 | 8/2011 | Ossart | |
| 2012/0206155 A1 | 8/2012 | Wang et al. | |
| 2012/0244608 A1 | 9/2012 | Selker et al. | |
| 2013/0171723 A1 | 7/2013 | Terentiev et al. | |

FOREIGN PATENT DOCUMENTS

| | | |
|---|---|---|
| DE | 39 05 158 | 8/1990 |
| EP | 1837640 | 9/2007 |
| EP | 1 952 971 | 8/2008 |
| EP | 2503320 | 9/2012 |
| WO | WO 98/52629 | 11/1998 |
| WO | WO 2004/109270 | 12/2004 |
| WO | WO 2005/068059 | 7/2005 |
| WO | WO 2005/108549 | 11/2005 |
| WO | WO 2008/016411 | 2/2008 |
| WO | WO 2010/010313 | 1/2010 |

OTHER PUBLICATIONS

US Office Action dated Dec. 22, 2010 issued in U.S. Appl. No. 11/728,560.
US Final Office Action dated May 24, 2011 issued in U.S. Appl. No. 11/728,560.
US Notice of Allowance dated Jul. 11, 2011 issued in U.S. Appl. No. 11/728,560.
US Office Action dated Jan. 30, 2013 issued in U.S. Appl. No. 13/134,157.
US Office Action dated Aug. 19, 2013 issued in U.S. Appl. No. 13/134,157.
US Final Office Action dated Jan. 22, 2014 issued in U.S. Appl. No. 13/134,157.
EPO Search Report, dated May 3, 2013, issued in EP 12 16 1078.
European Office Action dated Oct. 6, 2009 issued in EP 07 795 356.
European Office Action dated Aug. 9, 2010 issued in EP 07 795 356.
European Office Action dated Feb. 18, 2014 issued in EP 07 795 356.
SG Search Report, dated Nov. 7, 2012, issued in SG 201202181-2.
European Office Action dated Aug. 16, 2013 issued in EP 12 16 1078.
European Office Action dated Nov. 15, 2013 issued in EP 12 16 1078.
PCT International Search Report and Written Opinion dated Oct. 29, 2007 issued in Application No. PCT/US2007/012498.
Hartzel, William J. (Apr. 19, 2007), Materials of Construction for Single-Use Bioprocessing Systems, Innovations in Pharmaceutical Technology, pp. 46-50.
Lakowicz, Joseph R. (2006), Principles of Fluorescence Spectroscopy (3rd ed.), ch. 3, pp. 88-89.
Müller, G. et al. (Apr. 1, 1981), Quantitative ATR Spectroscopy: some basic considerations, Applied Optics vol. 20, No. 7, pp. 1182-1190.
Shenton, M J et al. (Sep. 5, 2001), Adhesion enhancement of polymer surfaces by atmospheric plasma treatment, J. Phys. D. Appl. Phys. 34, pp. 2754-2760.
Thermo Scientific HyClone BPC Products and Capabilities 2008/2009 (2008), Thermo Scientific.
Timmins, Mark et al., Bioprocess Bags Integrally Equipped with Oxygen or pH Sensors, http://www.wissmess.de/uploads/produktdokumente/1252325244Polestar O2 iDot Rocker Bags Poster %28IBC 2008 Single Use%29.pdf.
US Office Action dated Sep. 2, 2015 issued in U.S. Appl. No. 13/134,157.
EPO Opposition, dated Jul. 7, 2015, issued in EP 12 16 1078.
CN Office Action, dated Mar. 30, 2015, issued in CN 201210110032.8.
"Modifizierung von Kunststoffoberflächen durch Niederdruckplasmabehandlung zur Verbesserung der Adhäsionseigenschaften", Manfred Rasche in: Adhäsion, 1986 (3), pp. 25 to 28 (translation attached).

* cited by examiner

COMPOSITE SENSOR ASSEMBLIES FOR SINGLE USE BIOREACTORS

RELATED APPLICATIONS

This application claims priority under 35 USC 119(e) from, commonly assigned Provisional Application Ser. No. 61/465,849 filed Mar. 25, 2011 and Utility Application Ser. No. 13/134,157 filed May 31, 2011 the entire disclosures of which are incorporated herein by this reference. This application is a continuation-in-part of U.S. patent application Ser. No. 13/134,157 filed May 31, 2011, titled "COMPOSITE SENSOR ASSEMBLIES FOR SINGLE USE BIOREACTORS", which is a continuation-in-part of U.S. patent application Ser. No. 11/728,560 (now U.S. Pat. No. 8,008,065 issued on Aug. 30, 2011), filed Mar. 26, 2007, and titled "DISPOSABLE BIOREACTOR VESSEL PORT," which claims the benefit of U.S. Provisional Patent Application No. 60/835,329, filed on Aug. 2, 2006, titled "DISPOSABLE BIOREACTOR VESSEL."

BACKGROUND OF THE INVENTION

The increasing popularity of single-use systems for bio-processing is apparent in the market place and can be readily understood by considering a typical biotech manufacturing facility. The infrastructure required to implement a facility using traditional glass/steel bioreactors, mixers, and purification systems is substantial, and the time and expense required to construct such bio-process systems can be immense. The requirement that both the equipment itself and also the ingress and egress tubing utilize inert materials such as 316L electro-polished stainless steel requires a large initial investment and the bioreactors, (i.e. bio-process vessels) mixers and down-stream processing equipment (e.g. chromatography skids, filtration systems) all have a considerable footprint. In contrast, the size and form factor of single-use platforms generally permits easier storage and re-configurability when compared to traditional, rigid glass/steel solutions. Other advantages of single use systems include a lower support infrastructure and time savings over traditional designs including specifically the reduction in preparation and sterilization time, the reduced need for purified water for cleaning the vessel after a run, and the significantly reduced post run maintenance time. Additionally, single use systems and their associated plastic tubing lend themselves to being re-configured and validated quickly and efficiently as manufacturing or process requirements change. In the context of the present invention we will focus primarily on single-use bioreactors, but the principals apply generically to any of the aforementioned single-use equipment used in bioprocessing, both in the upstream processing (USP) and downstream (DSP) processing arenas.

Although a number of different styles of single use bioreactors have been conceived and introduced into the marketplace, two types currently predominate. The first type of single-use bioreactor to become commercially popular is generally referred to as the "pillow" or "rocker" bag style, and is described, for example, in U.S. Pat. No. 6,190,913 the teaching of which is incorporated herein by this reference. This style of bag can be constructed from a variety of different polymeric materials, but generally speaking, low or ultra low density polyethylene (LDPE) and ethylene/vinyl-acetate (EVA) copolymers are currently among the most common materials for at least the innermost layer of the bag, i.e., the bag surface which is in contact with the aqueous growth medium. Other materials sometimes used in the construction of the single-use bioreactor vessels include high density polyethylene (HDPE) and Kevlar (Poly-paraphenylene terephthalamide). The pillow or rocker type of single-use bioreactor utilizes a wave motion induced by movement of a bag support platform which generally rocks about a single axis to both mix and sparge (aerate) the contents of the bioreactor. While the rocker type single-use bioreactor bag has enjoyed some marketplace success, to date one major issue has been the lack of robust, single-use sensors that can be integrated into these rocker bags and preferably be radiation sterilized together with the bag. By robust, we mean accurate, gamma or beta radiation stable and capable of being used for real time (real time within the speeds or time responses required for bioprocessing) e.g. providing 1-3 second sampling for process monitoring and control for at least 21 days. The pillow or rocker bag is not the only type of single-use bioreactor vessel in use today. There are also single-use polymeric hard shell bioreactors that functionally imitate small scale glass vessels, and also larger scale single-use, plastic liner bags that fit inside both rigid pilot and production scale glass/stainless steel stirred tank bioreactors (see e.g., U.S. Pat. No. 7,384,783 the teaching of which is incorporated herein by this reference). The larger liner bags are typically constructed of multi-layer film laminates that also utilize ultra low density polyethylene or EVA for at least their innermost layer.

By way of example, FIG. 6 shows the construction of the CX-14 film used by Thermo Fisher Scientific for bioreactor vessels. Sensors are generally introduced into these larger single-use bioreactors through lateral ports. Both pillow (rocker) bags and liner bags can be considered to be "polymeric bioreactor vessels" for purposes of the utilization of the bioprocess monitoring assembly of the present invention.

One key issue affecting polymeric bioreactor vessels and other types of single-use equipment in both upstream and downstream applications in general has been the method by which to introduce sensors and ancillary monitoring equipment or assemblies that require multiple different materials (e.g.: mechanical assemblies). The sensors (both single-use and traditional multi-use) are often introduced through the type of prior art port shown in FIG. 1 (see e.g. published application US2006/0240546) or as is shown in FIG. 2 of this application specifically for use with a rocker bag. The port shown in FIG. 1 can be used to introduce into the vessel a monitoring assembly which allows the use of different types of sensing elements while the port shown in FIG. 2 is generally restricted to fiber optic based, single-use sensor systems. We use the term "port" herein to denote a part of our assembly to make it clear that we are replacing these prior art port and component assemblies compromised of these separate components. It should be noted, however, in the invention described here that there really is no longer a port or a separate monitoring component which enters into the vessel through said port. The concept of a port dates back to glass and stainless steel bioreactors where the ports were comprised of threaded openings in the headplate or the actual vessel wall and into which sensors or other components were secured by a threaded cap with an o-ring seal. A more accurate analogy here would be if the assemblies were welded into the stainless steel bioreactor wall or the steel headplate in order to effect a seal.

The prior art port shown in FIG. 1 is typically made of a material that is similar to the surface of the bag that it is in contact with, as this allows it to be readily fused (e.g., thermally or ultrasonically welded) to the bag surface. The port shown in FIG. 1 is comprised of a cylindrical tube 10 and a flange 11. This type of port uses a mechanical seal to prevent leakage around the normally cylindrical sensor or other object introduced into the tube portion of the port. This mechanical seal can be a friction fit created by surface to surface contact over a relatively large area as shown in FIG. 3 (see published application US 2006/0240546). FIG. 3 shows in more detail how a cylindrical object (e.g., a conventional 12 mm diameter electrochemical dissolved $O_2$ (DO) or pH probe or aseptic connector like a KleenPak™) 34 fits into the tubular member 31 with a large contact area 33. This prior art port has a feature 32 that emulates an O-ring and an annular flange 35 which is welded to the liner of the single use bioreactor vessel. Similarly, the port can actually utilize an O ring seal as shown in FIG. 4, which shows a single use, free space optical assembly (e.g., single use sensor sheath) 41 installed in tubular port member 42 with a weldable polymer flange 43. The O-rings 44 are shown as residing in grooves 45 in the port tubular member. While these port designs can generally provide an air and water tight seal between the port and introduced assemblies, a significant amount of time is required to qualify and test these assemblies (e.g.: validate them for cGMP use) and they cannot be simply and directly assembled when manufacturing single-use polymeric bioreactor vessels. Additionally, there are circumstances where it is difficult to design a suitable port assembly to support the sensor assembly. This is especially true in the case of rocker type single-use bioreactor bags where there are drawbacks to using fiber optic based single-use sensors, but introducing an optimally designed free space based optical sensor assembly as described in U.S. Pat. No. 7,489,402, the teaching of which is incorporated herein by this reference, might require a larger port. However, a large port can put stress on the bag materials and is therefore difficult to construct such that the integrity of the bag can be assured while at the same time maintaining a leak free seal.

A preferable method of introducing sensor assemblies, (or other type of monitoring assembly) into single-use bioreactor vessels would be to simply weld these assemblies directly into the bags in a manner similar to the way that prior art ports and vents are presently attached to single-use bag liners. To date, this has not generally been feasible for most sensors or sensor assemblies. The reasons for the inability to implement such a solution for introducing sensors and other accessories into single-use bioreactor vessels or other single-use equipment include the fact that the bags or liners are generally made from laminated films where the inner layer is typically a high surface tension polymer such as ultra-low density LDPE or EVA; while the material used for the sensor assemblies (e.g.: whether a free space optical sensor, or electrical sensor) is generally needs to be a polymer such as a polycarbonate, cyclo-olefin, copolyester, or other thermo plastic that can be either transparent or opaque, substantially rigid, can meet USP Class VI standards, and in particular, can withstand the 50 kGy of gamma or beta radiation as is normally used for sterilization without a significant change in its physical or optical properties (e.g., the materials cannot become brittle or change opacity). The laminated films used to make the bags or vessel liners can be readily welded together, and although the prior art ports which are typically constructed from materials matching the inner layer of the single-use bioreactor (e.g.: LDPE, EVA, PVDF, or other polyolefin) can also be welded to the bag or liner, the optimal material for the sensor assembly itself cannot be readily welded to the film liner materials or to a port of the same material as the liner (See: "*Materials of Construction for Single-Use Bioprocessing Systems*", William Hartzel, *Innovations in Pharmaceutical Technology*, p 46, April 2007). We have found that the two materials i.e. the sensor assembly and the bag liner cannot be melted or glued together without altering the surface of at least the contact layer of the liner and generally without altering both material surfaces. Therefore, the ability, as is enabled by the current invention, to construct complex assemblies that can be welded directly to the bag provides important new possibilities for putting sensors or assemblies in single-use bioreactor vessels and addresses the many issues present with existing sensor port designs. In addition, in order to fully enable the single-use paradigm and process optimization on a global scale, the automation software, hardware, and single-use sensors must be expanded from upstream processing (USP) units such as mixers and bioreactors to also encompass downstream bioprocessing (DSP) tools such as chromatography assemblies and filtration skids which utilize similar films. The advent of flexible, modular equipment with integrated data historization would allow the collection of a unified set of process data from buffer mixing to the final ultra-filtration of the bioprocess product. The availability of data from sensors of specific process modules (e.g., mixer, bioreactor, and different process configurations, especially on the downstream side), would allow users to develop models for each process step and the interactions therein. Once sufficient information becomes available from the database, the bio-process engineer could optimize the entire process end-to-end and implement yield modeling.

As used herein the term bioprocess vessel is intended to include both USP and DSP tools. In DSP the equipment would ideally implement single-use sensors fabricated using the manufacturing processes of the present invention as described herein to either replace traditional sensors and/or enable new additional analytical capability. DSP equipment that utilizes film technology similar to that utilized in USP polymeric bioprocess vessels is described in U.S. Pat. No. 7,935,253. Ideal "smart" sensors for the DSP as well as the USP would have the capability of being pre-calibrated and gamma or beta irradiation sterilized along with the bio-process vessel itself. In this way the sensors would arrive enclosed in the transport container together with the bioprocess vessel. Thus, the entire system arrives sterile, thereby minimizing operator time during process setup. For example, in downstream applications, there is also a significant need for measuring pH and temperature, as well as optical density and product purity (e.g., viral load, biological impurities). In DSP sensor design, the ability to combine composite materials is particularly important as the optical requirements in the ultraviolet range further significantly limit the materials choices, and where requirements on extractables and leachables are becoming ever more stringent. Furthermore, as the size of single-use mixers, bioreactors, and DSP equipment increases to meet capacity, the risk of leakage from a standard sensor/port configuration increases with the greater pressure inside the container. This ability as provided by the present invention to utilize material combinations that were previously considered incompatible from a bonding perspective so as to provide an impermeable seal is an important enabling factor in both DSP and USP.

BRIEF DESCRIPTION OF THE DRAWINGS

FIGS. 1-7 are prior art while

FIG. 1 shows a prior art port design.

FIG. 2 shows the typical prior art method of introducing fiber optic based sensors into a single-use rocker bag.

FIG. 3 shows a prior art port design with a seal based on a friction fit.

FIG. 4 shows a prior art port design with sealing based on an o-ring compression seal.

FIG. 5 shows another version of a prior art port that utilizes fiber optic delivery and collection of the optical signal.

FIG. 6 shows the construction layers of the Thermo Fisher CX-14 bioreactor film

FIG. 7 is a diagram showing yet another version of a prior art port that utilizes fiber optic delivery and collection of the optical signal.

FIG. 8 is a top lateral view of a sensor-unit for rocker bags in accordance with the present invention that includes both optical and thermal sensor windows.

FIG. 9 is a cross-sectional view of a sensor unit in accordance with the present invention FIG. 10 shows a composite sensor assembly i.e. the sensor unit and the port in accordance with the present invention that is thermally welded to a single-use bioreactor bag.

FIG. 11 shows a partial interior view of a free space optics sensor assembly in accordance with the present invention that can advantageously replace current prior art port designs on a single-use stirred tank liner bag.

FIG. 12 is an exterior view of the sensor assembly of FIG. 11.

FIG. 13 is a profile view of an optical sensor assembly in accordance with the present invention suitable for optical scattering or absorption measurements.

FIG. 14 is a cross sectional views of a composite optical sensor assembly in accordance with the present invention, (in this instance an ATR spectroscopic device).

FIG. 15 is a cross sectional view of a composite optical sensor assembly in accordance with the present invention such as an ISFET where the optical device is in contact with the contents of the bioreactor vessel.

FIG. 16 is a cross sectional view of another type of composite optical sensor assembly in accordance with the present invention suitable for utilization of NIR or Raman spectroscopic interrogation of the vessel contents.

FIG. 17 is a cross-sectional view of drive assembly from U.S. Pat. No. 7,384,783. Such a drive assembly is substantially improved if fabricated from a combination of materials which can only be bonded utilizing the process of the present invention.

DETAILED DESCRIPTION OF THE INVENTION

The fiber optic based fluorescence sensors currently used in single-use bioreactors are known to suffer from a number of limitations including the following:
1. Accelerated photo-degradation leading to limited lifetime and/or measuring accuracy/capacity;
2. Sensitivity to ambient light;
3. Sensitivity to movement or physical perturbation.

Figure 3:
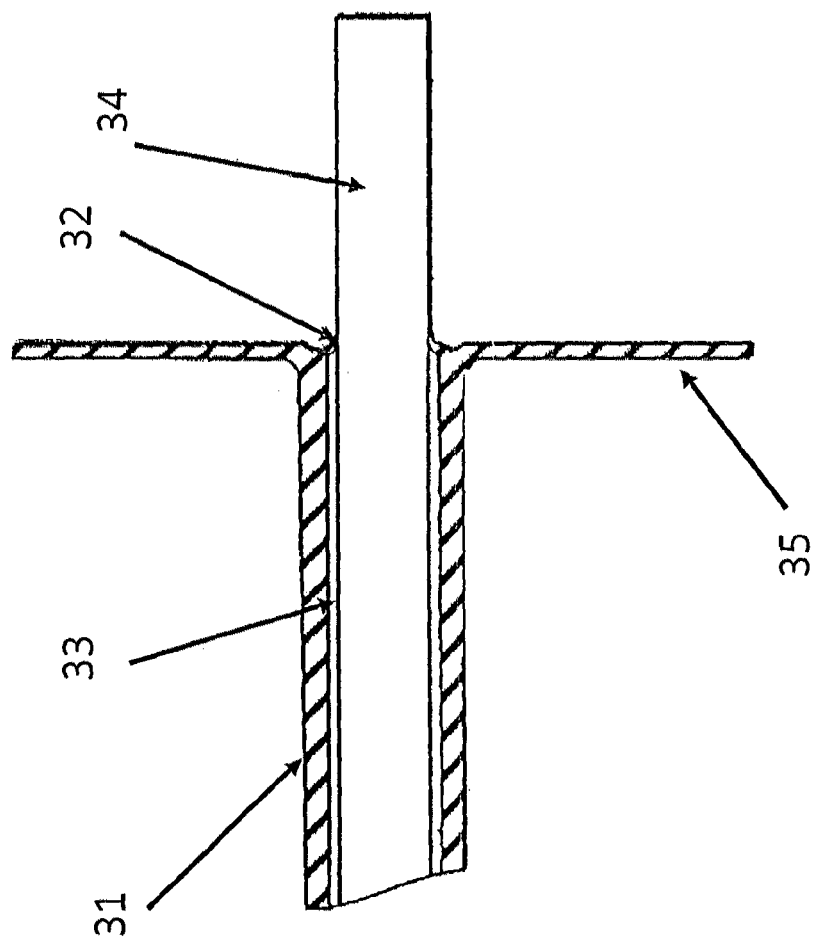
Figure 4:
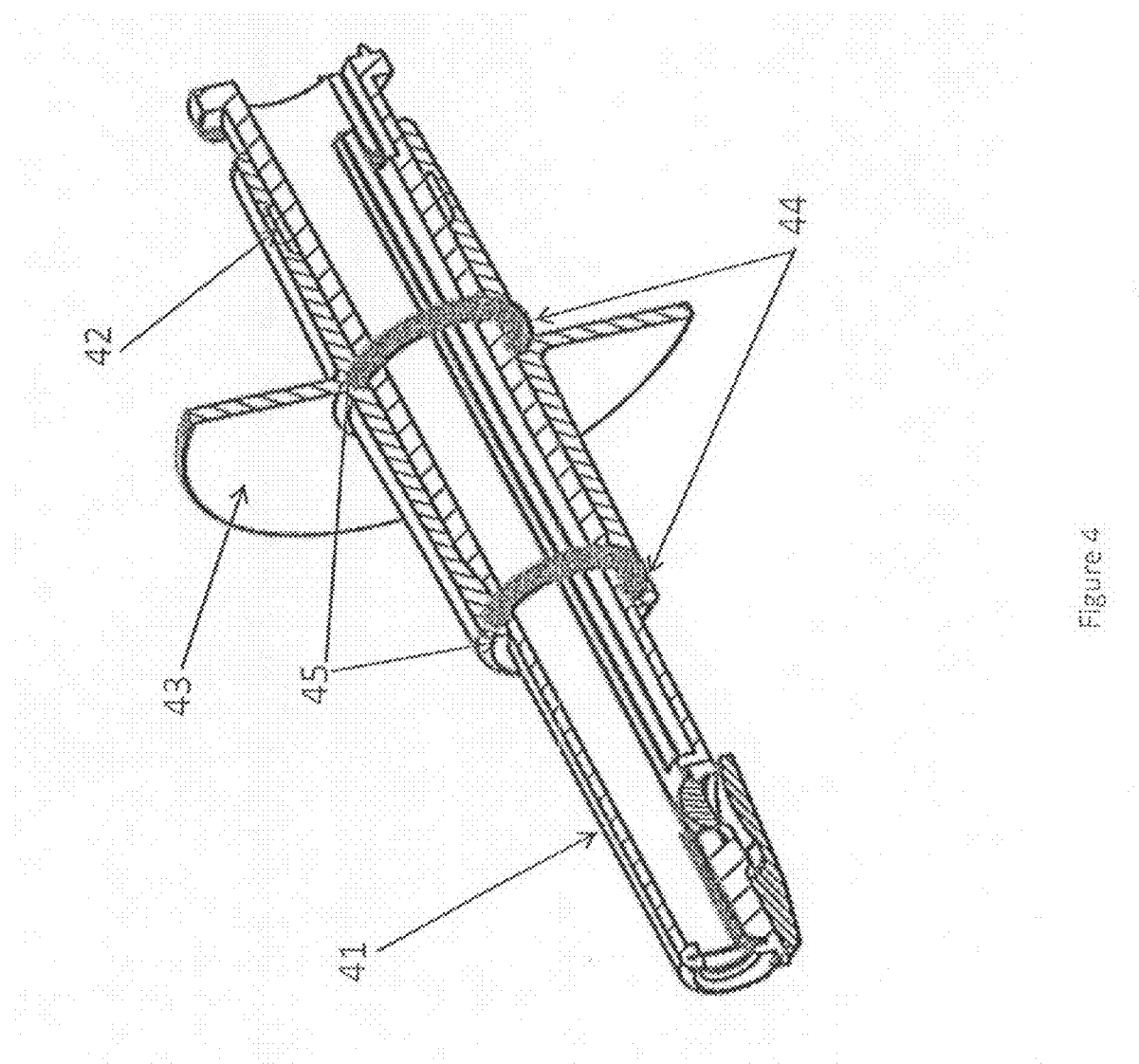

Stirred tank single-use bioreactor liners currently utilize ports configured, for example, as shown in FIGS. 3 and 4 to introduce sensors and/or sampling systems. However, these ports limit the form factor and shape of the sensor that can be utilized.

Figure 1:
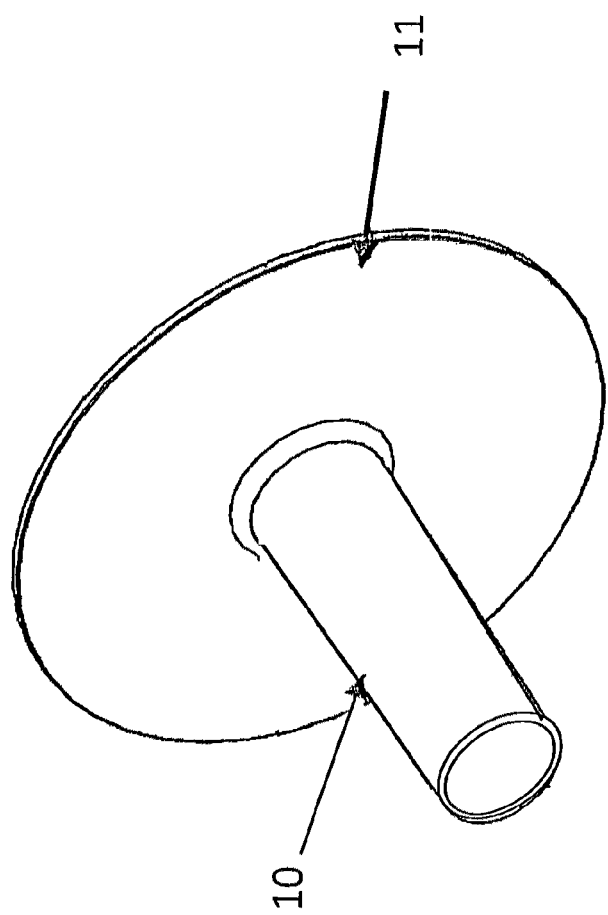
Figure 2:
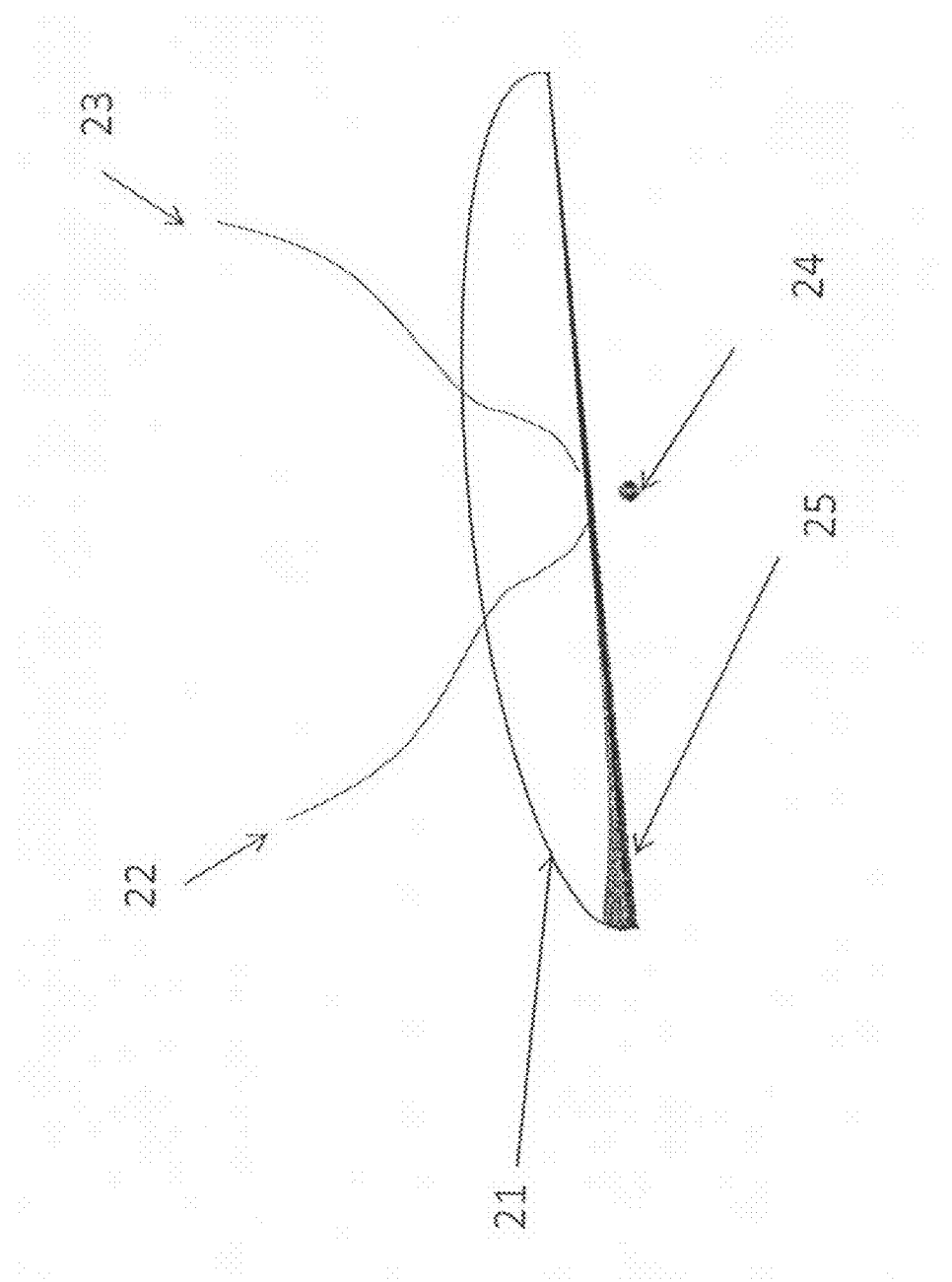

In the specific case of rocker type single-use bags, the fiber optic based sensors suffer significant limitations due to the method by which they are introduced into the bag. As shown in FIG. 2, the DO (dissolved oxygen) and pH fluorescent sensor spots are attached to the end of fiber optic assemblies 22 and 23. These fibers are introduced through the wall of the rocker bag 21, typically near the axis of rotation 24. As shown in FIG. 2, the fiber optic cables are generally brought in through the top of the rocker bag and the sensor at the end of the fiber optic cable is immersed in the bioprocess media at the bottom of the bag, in a fashion similar to a clunk line in a fuel tank. As the vessel rocks back and forth to the maximum angle, the fluid 25 moves to one or the other end of the vessel and can thus cause the sensor spots to become uncovered. As can be seen, this arrangement can cause the sensor spot to be exposed to the headspace gas (as opposed to being continuously immersed in the aqueous bioprocess media) during a rocking cycle, as well as being exposed to ambient light which can accelerate the photo-degradation of the sensor. This is because rocker vessels are generally filled to less than half of their capacity so that the liquid collects in the corners of the bag during the transition end points of the rocking cycle leaving the optical sensors situated near the middle of the bag uncovered for a fraction of each rocking period.

Sensor "spots" are typically comprised of fluorescent dyes (see J. Lakowicz, *Principles of Fluorescence Spectroscopy, $3^{rd}$ Edition, Springer*, 2006) impregnated in inert, porous materials like cellulose or ormosil glass, and the target analyte in question diffuses into the sensor spot and changes the fluorescent properties of the dye(s). The diffusivity of a gas into the sensor spot is far higher than that of a liquid, so even a brief (temporal) exposure to the headspace gas can significantly affect the sensor reading and thereby cause significant measurement inaccuracies. For example, if the response time (90% response) of the sensor spot in liquid is 30 seconds and the DO concentration in liquid is 30% Sat (saturated), and the response time in the gas (headspace) phase is 3 seconds and the DO is >100% Sat it is easy to see how even brief exposure to the headspace can have a large adverse effect on the accuracy of the measured DO value.

Figure 5:
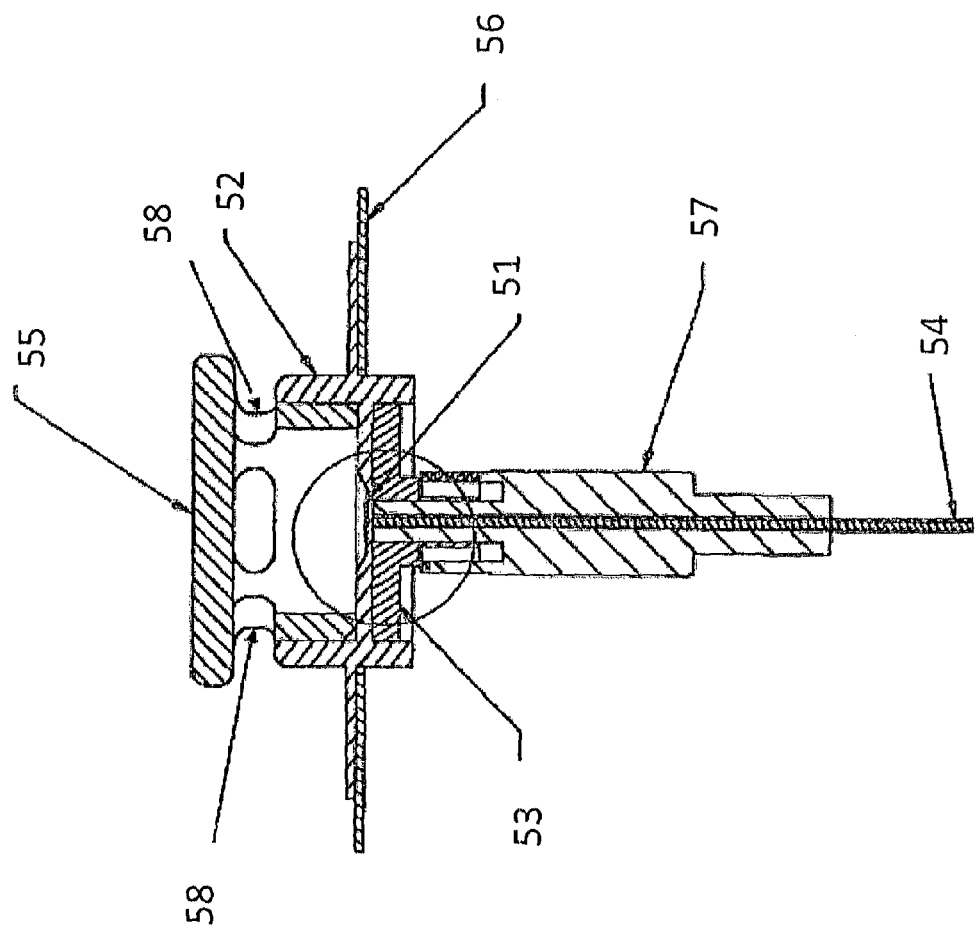

Several attempts have previously been made to address the aforementioned issues. One proposed solution (see for example U.S. Pat. No. 7,824,902) to the ambient light issue in single-use bioreactors that utilizes fiber optic based sensors is shown in FIG. 5. Here 51 is the oxygen sensitive fluorescent dye, 52 is a biocompatible material such as low density polyethylene that comprises a port which is welded into the bioreactor's lining 56. The fiber optic cable is shown as 54 while 55 is a shield that seeks to prevent ambient light from directly impinging upon the photosensitive dye while still allowing fluid to flow freely around the sensor spot. The fiber, 54, is shown as locking to a ferrule, 57, which is part of the port assembly, while 58 indicates openings into a receiving vessel which sits above the bag liner. This solution allows for affixing the fiber optic assembly and sensor spot to the single-use bioreactor and also allows for a light shield to limit the ambient light that impinges upon the spot. This would be of specific importance to sensor spots like pH spots which typically cannot support an opaque coating since there are few, if any, opaque, USP Class VI qualified coatings that allow ions (e.g., H$^+$) to pass through to the sensor spot.

Figure 6:
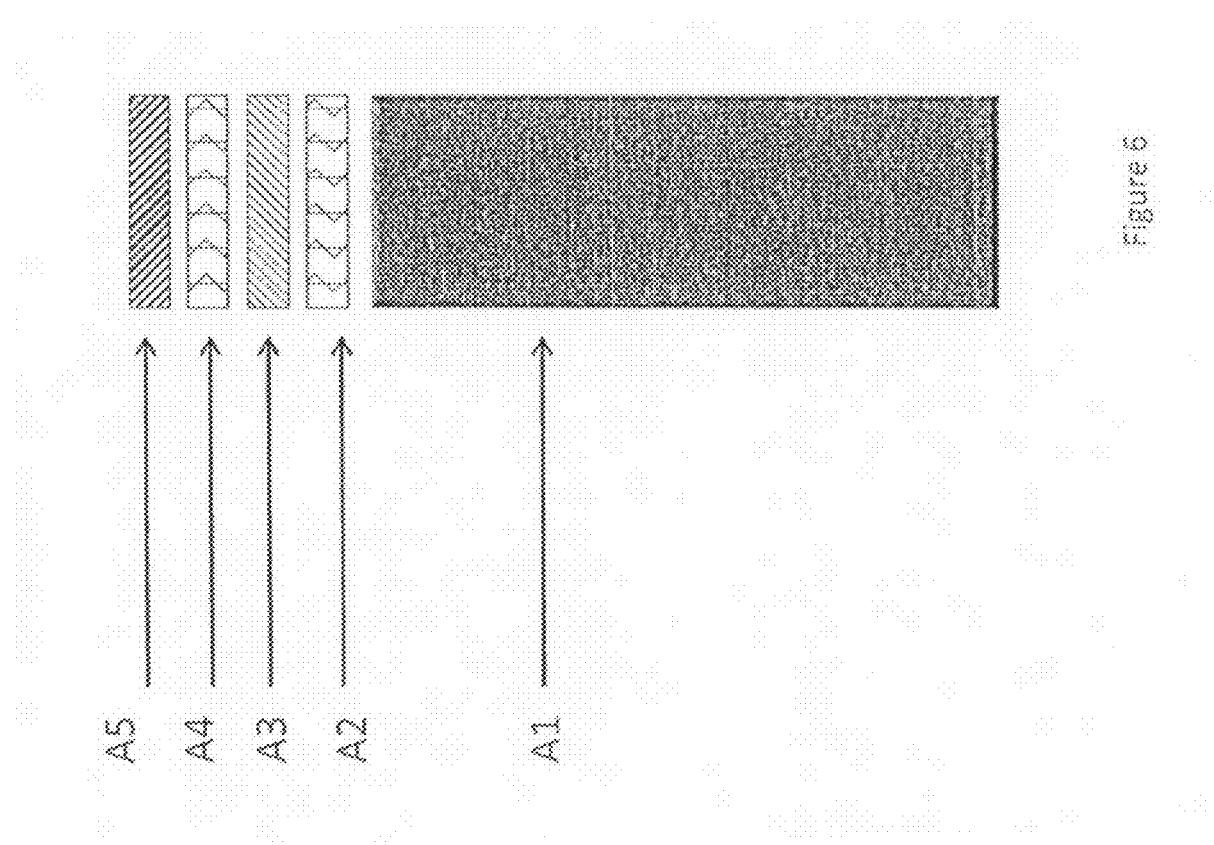

The rocker type bags and the liner type single-use vessels are generally constructed from laminated films as shown in FIG. 6. This figure shows the Thermo Fisher CX-14 film where the layer in contact with the bio process liquid is A1 (low density polyethylene, 10.4 mil thick) followed by layer A2 (a 0.9 mil thick "tie layer" which bonds A1 and A3), and layer A3 (Ethylene-vinyl alcohol copolymer "EVOH", 1.0 mil thick), and layer A4 (another 0.9 mil thick "tie layer" which bonds A3 and A5), and finally A5 (polyester, 0.8 mil thick). Reference: *Thermo Scientific Hyclone BPC Products and Capabilities* 2008/2009. Not all laminated films employed in single-use applications need to employ these materials or this number of layers.

Figure 7:
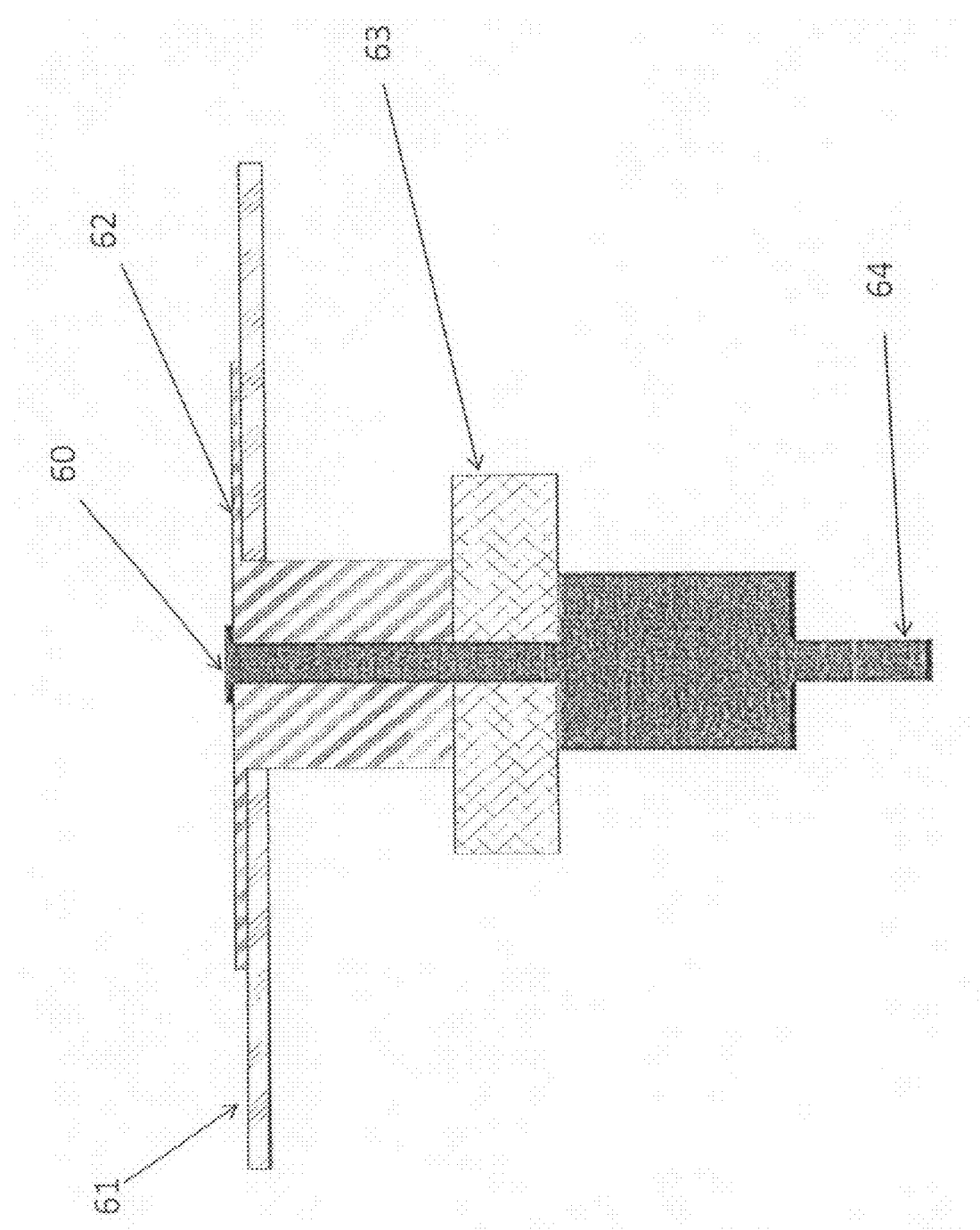

Other prior art attempts have been made using a similar method to minimize the time that the sensor is uncovered in a single-use rocker bag by bringing the fiber optic sensors in through a port in the bottom of the bag as shown in FIG. 7 (taken from: *Bioprocess Bags Integrally Equipped with Oxy-* gen or pH Sensors, Mark Timmins, Si Chen, Aaron Loren, Steven Archibald, Kurt Christoffersen, Jean-François Hamel, and James Kane). The fiber optic cable, 64, is connected to a standard fiber optic connector, 63, which is embedded in a port 62 which is thermally welded to the inner film layer (normally LDPE or EVA or similar inert layer) of the single-use bioreactor 61. The sensor spot, 60, is attached to the end of the fiber optic cable. The spots are at, or slightly above the bottom of the bag. However, we have found that with this design for low liquid volumes the spots can still become uncovered at the maximum rocking angle and speed. Also, in this approach there is no protection for the sensor spots from the effects of ambient light. Thus, in this approach the sensor spots can still be exposed to both headspace gas and to ambient light thereby allowing the measurement fidelity to be compromised and the sensor spot to be subject to photo-degradation.

An optimal system would avoid the known issues of fiber optic cable based optical sensors: it would minimize ambient light exposure, and it would also eliminate the possibility of having the values measured by the sensor when immersed in liquid being corrupted by exposure to headspace gas phase contributions. Ideally, the system would also be capable of being attached to the bag during the normal course of construction using the same equipment (e.g.: thermal welding equipment, seam sealers) used to make the bag. The present invention successfully addresses these issues.

We have found that illumination based photo-degradation issues can be addressed by using a free space optics based sensor design. The use of free space optics and the details of such sensors and their advantages are described in U.S. Pat. No. 7,489,402 the entire teaching of which is incorporated herein by this reference. A fundamental concept put forth in this patent, is that the drift in measurement accuracy in phase fluorimetric sensor systems due to photo-degradation can be significantly reduced (in many cases to a level that is not measurable) by minimizing the amount of light used to illuminate the sensor spot(s). Free space optics and an appropriately sized photo-detector can, in virtually all circumstances, collect far more light from a fluorescent sensor spot than can a fiber optic cable. As is known, fiber optic systems are limited by fundamental physical laws as to how much light they can collect. The fundamental law of physics describing this issue is known as "conservation of brightness". This limitation also applies to free space optics, but the limitation's effects are nowhere nearly as severe. As a free space optical system can collect far more light (easily greater than a factor of 10 vs. a fiber optic cable) it therefore requires far less light to illuminate the fluorescent sensor and will therefore cause a far slower rate of photo-degradation. However, for optimally accurate results a method is needed to minimize or eliminate the exposure of the spot to the gas phase and also ensure that the entire spot always remain submerged, even for low fill volumes and to also protect the spot from exposure to ambient light.

Figure 8:
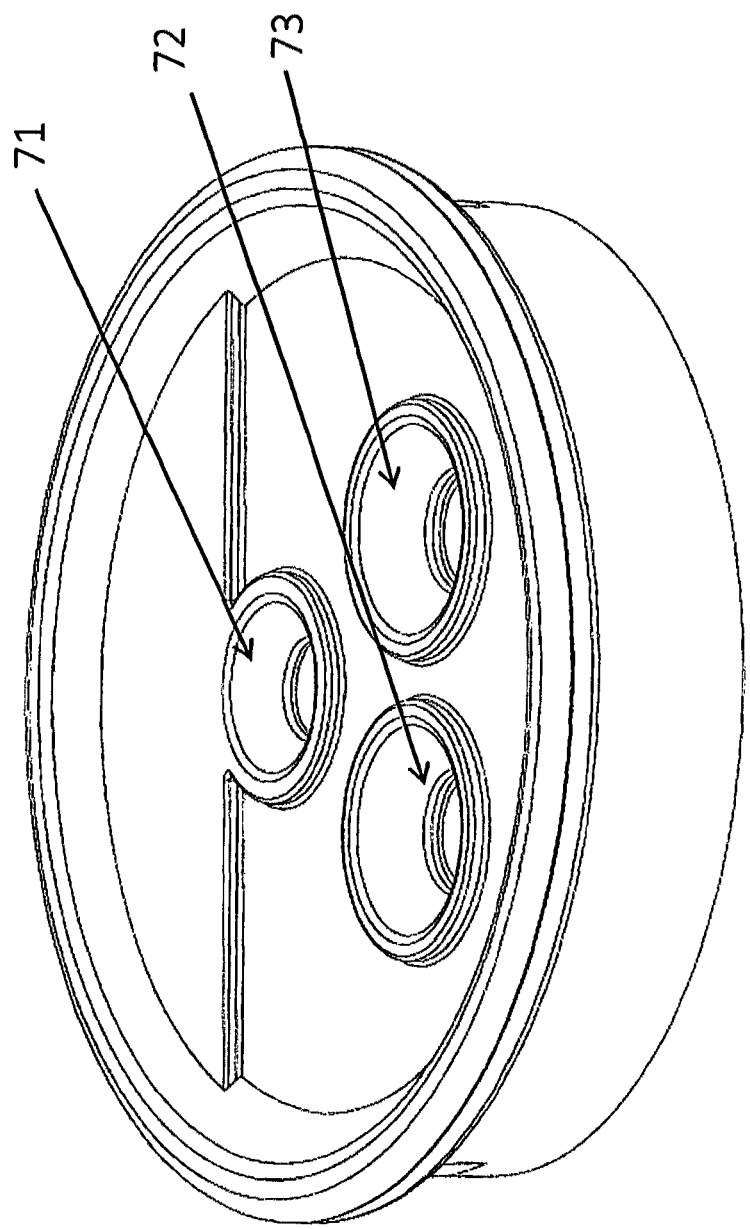
FIGS. 8-17 are illustrative of the present invention.
Figure 9:
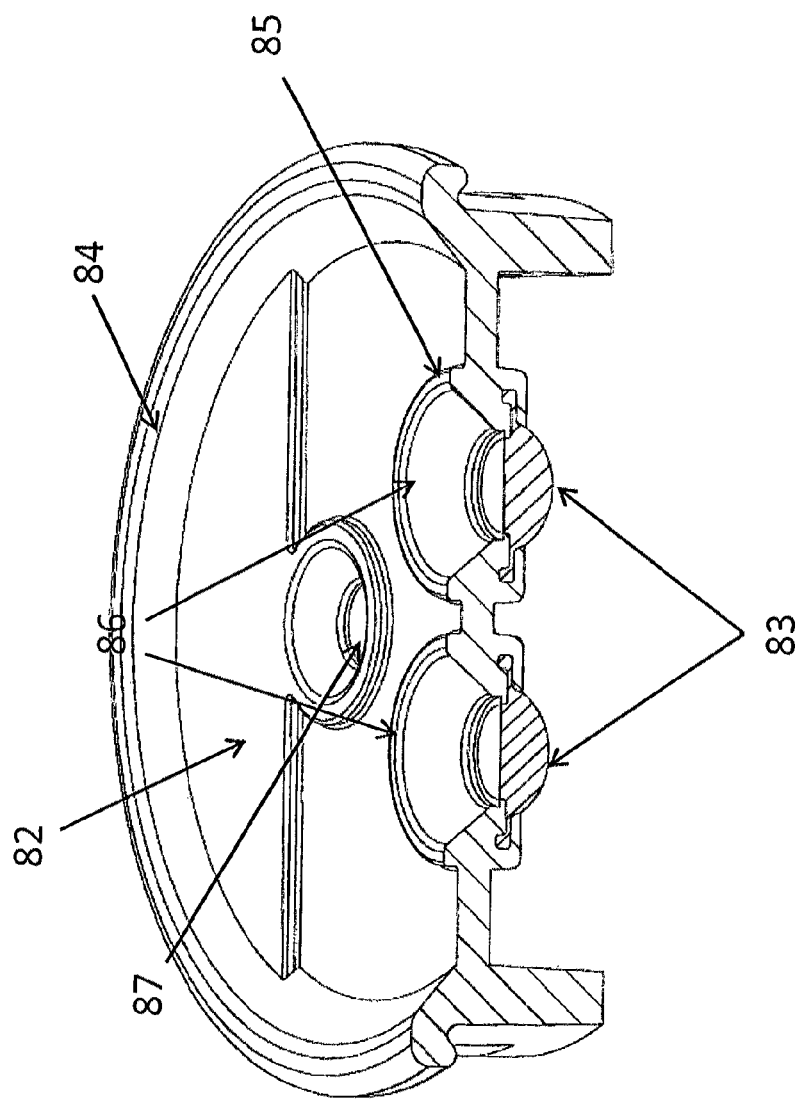
Figure 10:
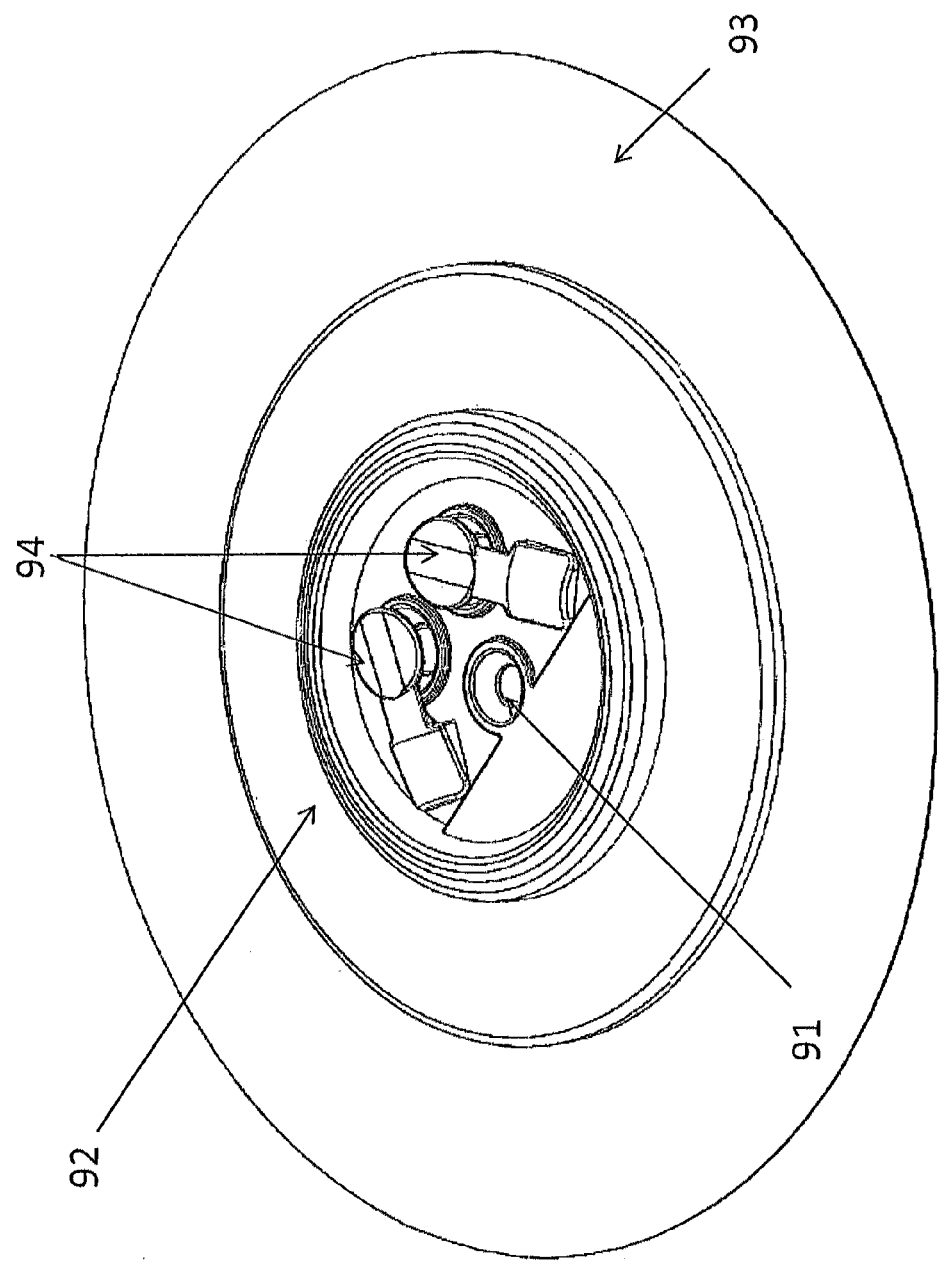

A sensor design in accordance with the present invention, which is particularly suitable for use in rocker bags, and which can be physically realized and practically implemented to avoid the aforementioned problems, is shown in FIGS. 8 through 10.

The composite sensor assembly of the present invention is suitable for use with a polymeric bioprocess vessel and also with downstream bioprocessing equipment, and comprises:
 i) a port comprising a high surface tension thermoplastic such as LDPE or EVA having a hollow tubular portion and a base plate portion, the base plate being fusibly sealable to the bioreactor vessel at a hole in the wall thereof;
 ii) a polymeric sensor (monitoring) unit including at least one electrical and/or optical measurement component (generally opaque when only optics are used). The sensor unit fits inside the bore of the hollow tubular portion of the port, and is adhesively retained therein using a special process in accordance with the present invention as described hereinafter. Preferably a plurality of measurement components will be present in the monitoring unit.

Figure 11:
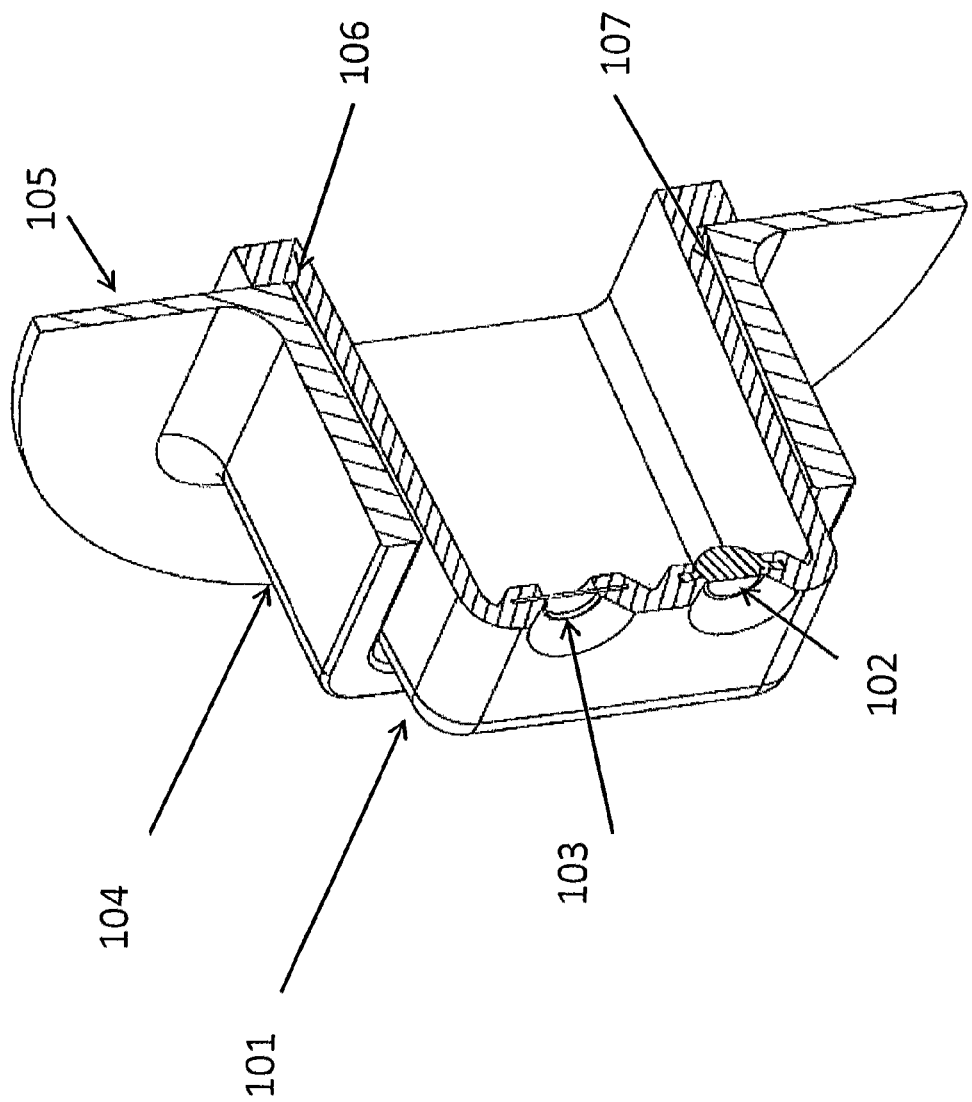
Figure 12:
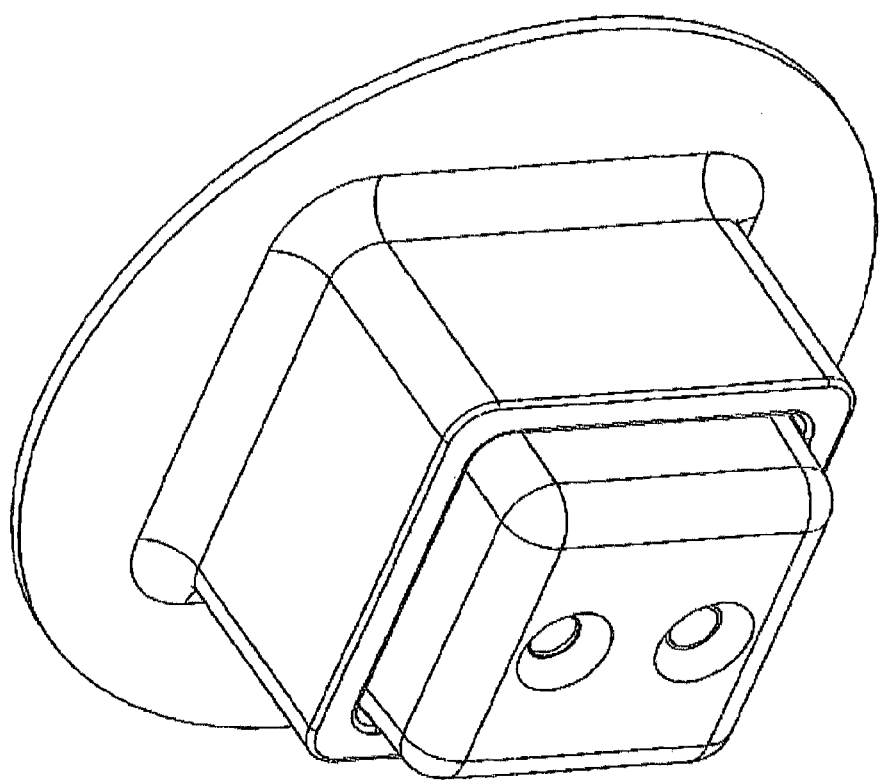

Although the port is shown as being cylindrical in shape and described as being "tubular" such terminology is not to be construed as requiring that either the tubular (hollow) portion of the port or the sensor unit be circular in cross section. Specifically, the sensor unit and the tubular (port) portion of the unit can have any geometric shape, provided that sensor unit can be sealably affixed to the port and that the base plate has an orifice which provides access to the biovessel contents. The port provides the sensor unit components with access to the contents of the bioreactor vessel, which components include means for providing incoming optical and/or electrical signals and means for collecting and transmitting measurement signals emitted by the sensor assembly components. For use with a rocker bag, the sensor unit is preferably (but not necessarily) circular and is generally dish shaped and includes a base portion and a concentric rim extending above the base. The sensor unit preferably has cup shaped depressions in the inner surface of the base thereof. Each of the monitoring components is situated in a separate cup shaped depression in the base of said sensor unit and each said cup shaped depression preferably includes a surrounding rim which extends above the inner surface of the sensor unit base. The cups containing optical sensor (monitoring) components will preferably have a light shield positioned over the top thereof. In current practice, although not required particularly in a free space optics sensor unit designed for use with a liner bag the probe will frequently be substantially cylindrical in shape and will be contained within the bore of the tubular portion of the port as shown in FIGS. 11 and 12 with the sensor unit again being adhesively retained therein using a special process as described hereinafter.

FIG. 8 shows the free space optical sensor unit in which the DO and pH spots are mounted in the recessed "cups" 72 and 73 which help maintain bioprocess fluid covering the spots at all normal angles of rocking and rocking speeds. The temperature is measured through a cup having a thin 316L electro-polished stainless steel plate shown as 71.

FIG. 9 is a cross-sectional view of a sensor unit in accordance with the present invention for use with a rocker bag showing the optically opaque sections of the sensor unit 82, as well as the optically transparent sections 83. The opacity is normally achieved by incorporating USP Class VI absorptive colorant into a normally transparent or translucent polymer. As shown, each sensor unit sits below the fluid surface in its own cup 85. Note that each of the cups 85 preferably has its own ridge 86 which alters the liquid flow through the cup and thereby reduces the collection of debris in the cup since the ridges create a flow pattern conducive to sweeping out debris. It should be noted that the entire sensor unit in certain preferred embodiments will also have a peripheral ridge 84 which serves to retain fluid inside the sensor unit. An additional benefit of the ridge is that it creates a fluid flow path which minimizes the collection of particulate debris (e.g.: dead cells or other precipitates) in the sensor containing cups 85. The temperature sensor containing cup 87 is normally slightly different in size and depth compared to the pH or DO sensor containing cups, but follows the same concept in that it has been designed to retain liquid. Instead of a free space optical sensor it utilizes a 316L electropolished plate for good thermal conductivity with the bioreactor fluid and also contains an RTD, thermistor or equivalent temperature sensor.

The materials chosen for the polymeric portions of the sensor unit, including the cups that hold the sensor spots will advantageously have the following characteristics:
- Stability (in optical and mechanical properties) after exposure to sterilizing gamma or beta radiation;
- Structural integrity;
- Low cost;
- Ability to meet USP Class VI standards;
- Animal component derived free;
- Ability to be molded;
- Optical opacity of the body of the sensor unit and optical transparency in the portions that need to transmit light.

The list of polymeric materials that meet the above criteria includes polycarbonates, cyclo-olefin copolymers, co-polyesters, polystyrene and other artworker known beta or gamma radiation stable thermo-plastics.

As previously mentioned the innermost layer of single-use rocker bags is generally constructed from LDPE or EVA because these polymers are chemically inert and non-reactive with biological materials and also are available as a USP Class VI film. Additional outer reinforcing and/or bonding layers are sometimes also present so that many bags include additional layers of other polymers in addition to the innermost LDPE or EVA polymer layer. Henceforth, we will generally refer to LDPE as the material used to construct the single-use bioreactor bag but the bag can alternatively be fabricated from one of the aforementioned materials or other suitable thermoplastic film meeting USP Class VI standards.

A central issue and problem that are addressed by the current invention is that most of the materials suitable for the sensor unit cannot be thermally or otherwise readily and effectively bonded to LDPE without subjecting at least the LDPE to surface preparation, and in many cases subjecting both the LDPE and the interfacing portion of the sensor unit to surface preparation. It is difficult to bond LDPE to dissimilar polymeric materials in a reliable, robust way that still allows the bonded part to withstand sterilization (typically by gamma or beta radiation) and also still meet USP Class VI standards. This makes it difficult to utilize the optimal materials from a free space optical device (or electrical device or device using optics, electronics, and/or chemical transducers) perspective for the sensor unit, while at the same time maintaining the ability to bond this part (the sensor unit) into the single-use bag. Therefore, it is not obvious how to simultaneously implement a sensor unit that meets the requirements for measurement (e.g.: long lifetime, good accuracy, functionality) and also sealingly integrate it into a single-use bioreactor vessel.

In order to create an optimal free space optical system for phase fluorimetry, materials meeting the aforementioned requirements must be used. Therefore, a bonding method that meets all the applicable requirements must be employed to bond the sensor assembly to the single-use bioreactor vessel. A variety of methods of surface preparation are known and some could in theory be employed with LDPE or EVA (see e.g., "Adhesion enhancement of polymer surfaces by atmospheric plasma treatment", M J Shenton, M C Lowell-Hoare, and G C Stevens, *Journal of Physics D: Applied Physics*, 34 (2001) 2754-2760). For example, it is possible to chemically etch the surfaces to be mated or alternatively to create a "meta-layer" where the surfaces are doped with materials that bond together more readily. While such methods enable the bag and the interfacing surface portion of a sensor assembly to be bonded together, there are very few choices of chemical etchants that will provide a product that meets USP Class VI standards. We have found that a more advantageous method that works for LDPE, EVA and most other poly-olefins or ethylene copolymers used for the inner surface layer of bioreactor bags is surface preparation of the mating surfaces of both that portion of the sensor assembly (which is fabricated from a polymer that is readily fusibly bonded to the bag) and the rigid sensor unit structure containing the free space optics, electronics, or a combination thereof by methods such as plasma cleaning, UV ozone cleaning or other approach that creates adsorption sites on the mating surfaces. As most single-use bags are manufactured by "welding" the parts together (using thermal methods, ultrasound, etc.), it is therefore advantageous to create a part (i.e., the sensor assembly of the present invention) that can be welded onto the vessel in the same fashion as conventional ports and vents.

Our invention therefore utilizes a port fabricated in part from LDPE, EVA or similar polymer suitable for bonding by known methods (e.g., thermal welding) to the single-use liner or rocker bag film (e.g. be readily bondable to the LDPE bioreactor bag inner layer surface) combined with a free space optical sensor unit fabricated from one of the aforementioned special polymers (e.g. polycarbonates, cyclo-olefin copolymers, copolyesters, and polystyrene). The port to bag and port to sensor unit when fabricated in accordance with the present invention provides an aseptic and fluid impervious seal. Following the aforementioned surface treatment of either (or preferably both) of the mating surfaces of the port and the sensor unit, we have found they may be advantageously and effectively bonded together using USP Class VI adhesives which include one or two part epoxy resins, UV curable epoxies, cyanoacrylates, silicones, or polyurethanes. In order to ensure that the chosen adhesives do not excessively cross-link and become brittle under gamma or beta sterilizing radiation, they can be examined and tested after radiation exposure in order to ensure that they qualify for this application in accordance with applicable USP standards.

The composite sensor assembly we describe herein uses the aforementioned surface preparation techniques to enable the bonding of an optical/physical component to an LDPE or EVA port which port can be subsequently welded using known methods into a single-use vessel fabricated from LDPE (or EVA). This method enables a far greater degree of freedom in the design of components that can be sealed into single-use bioreactors (or other single-use process equipment) which utilize materials such as LDPE or EVA having a high surface tension and that are therefore inert and also difficult to bond to dissimilar materials. This alleviates the need to insert the components through rigid or semi-flexible ports that are limited in shape and spatial extent. The unit in accordance with the present invention shown in FIGS. 8 and 9 is a sensor assembly in accordance with the present invention that allows for the use of fluorescent based optical sensor(s) and also, if desired, a temperature sensor (thermal probe). Moreover, this method can be applied to other different types of probes (monitoring devices) that are advantageously used with single-use process equipment including electrical sensors (e.g.: ISFETS) or other types of optical sensors based on spectroscopic methods (e.g.: near infra-red or Raman). FIG. 10 shows a composite sensor assembly in accordance with the present invention, i.e., the sensor unit is integrated with the port and fused to the bioreactor vessel wall. Additionally, this bonding method is not limited to a rocker type single-use bag or polymeric liner bags as the composite assembly of the present invention can be readily welded to any single-use polymer vessel, column, or container that requires sensors. Finally, this method does not compromise the USP Class VI classification of the materials, so that the combined product is still suitable for bio-processing applications.

As shown in FIG. 10, the sensor assembly which includes the sensor unit having optical sensor cups (shown as 72 and 73 in FIG. 8 and as 83 in FIG. 9) and a plate 91 with high thermal conductivity (e.g.: 316L electro-polished stainless steel), and which also meets USP Class VI standards and through which temperature can therefore be sensed or measured are affixed to the port base plate 92 (preferably fabricated from LDPE) with a suitable adhesive subsequent to plasma cleaning as previously described, and the assembly is then thermally welded to the bag film 93 (shown here in circular form). Optional light shields, 94 to avoid signal interference and photo-bleaching are also shown situated above the optical sensor cups. The light shield is also advantageously used on fluorescent sensor spots that cannot support or cannot otherwise be used with an opaque coating such as black silicone polymer. The light shield allows bioreactor fluid to flow to the sensor spot, but blocks a large percentage of the ambient light. This reduces the potential for photo-degradation of the sensor spot and also for interference with the optics and electrical amplification used in the fluorescent signal detection.

FIG. 11 shows one version of the composite sensor assembly of the present invention that would be particularly suitable for use with a single-use, stirred tank plastic liner bag. The sensor unit shown as part of the sensor assembly in FIG. 11 is comprised of a preferably at least partially opaque optical sensor unit that is constructed of a suitable USP Class VI, gamma radiation resistant, substantially rigid and animal component derived free polymeric material as previously described. Here 102 is a transparent component (e.g.: a lens) made from a similar material but without colorant added. A fluorescent sensor spot (not shown) is suitably placed on top of the optical component. Other optical sensor measurement techniques like NIR spectroscopy or Raman spectroscopy require no sensor spot. A suitable thermally conductive area (e.g., a 316L electro-polished stainless steel plate for temperature measurement) is shown as 103. The port 104 is suitably made from a material that is readily welded to the single-use bag liner and will preferably have a circumferential flange 105 to facilitate said bonding to the bioreactor bag. It is sometimes also desirable to have additional features in the sensor unit 101 and/or the port 104 (i.e., have an increased mating surface area or a ledge) such that when the port's inner surface (106) and the sensor unit's outer surface are prepared via plasma treatment, an adhesive such as platinum cured silicone 107 will readily adhere to both surfaces. The composite sensor assembly as shown in FIGS. 11 and 12 (an exterior, non-cutaway view of the sensor assembly of FIG. 11) utilizes a free space optical sensor unit, but is equally suitable for use with an electrical or chemical sensor unit.

Figure 13:
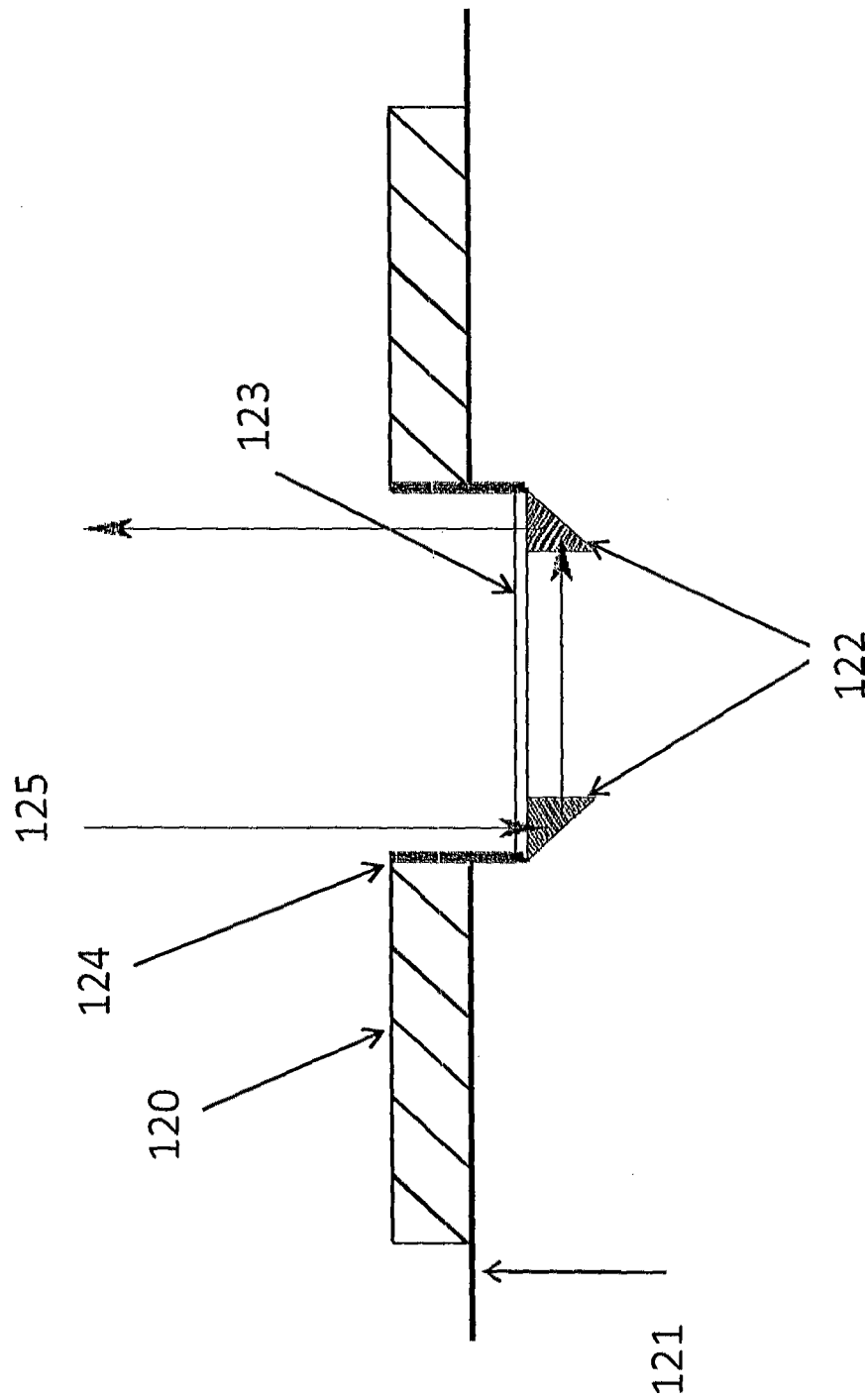

FIG. 13 depicts a profile view of a composite optical assembly particularly suitable for optical density measurements (using UV, near infra-red, or visible light) or optical absorption spectroscopy measurements. In FIG. 13, 120 is the liner compatible material (e.g.: LDPE), and 121 is the single-use bag film. The optical part of the composite assembly is comprised of the sidewall, 124, which is adhesively affixed to the liner compatible material 120, whereas 123 is the floor of the optical assembly and can suitably be of the same material as 124 or not depending on the optical properties required. Components 122 are optical prisms that are used to refract or reflect the light beam 125 beam across an optical gap. The prisms would typically be coated such that they reflect the light beam 125, as shown. The light traversing the gap in part determines the optical properties of the components utilized and therefore the material selection. The exact separation between the prisms (optical gap length) is determined by the absorption and scattering properties of the material that is intended to be characterized by this system. The processing of the optical signals can be by a photo-detector or power meter with a filter in front, or it can be by a spectrometer.

Figure 14:
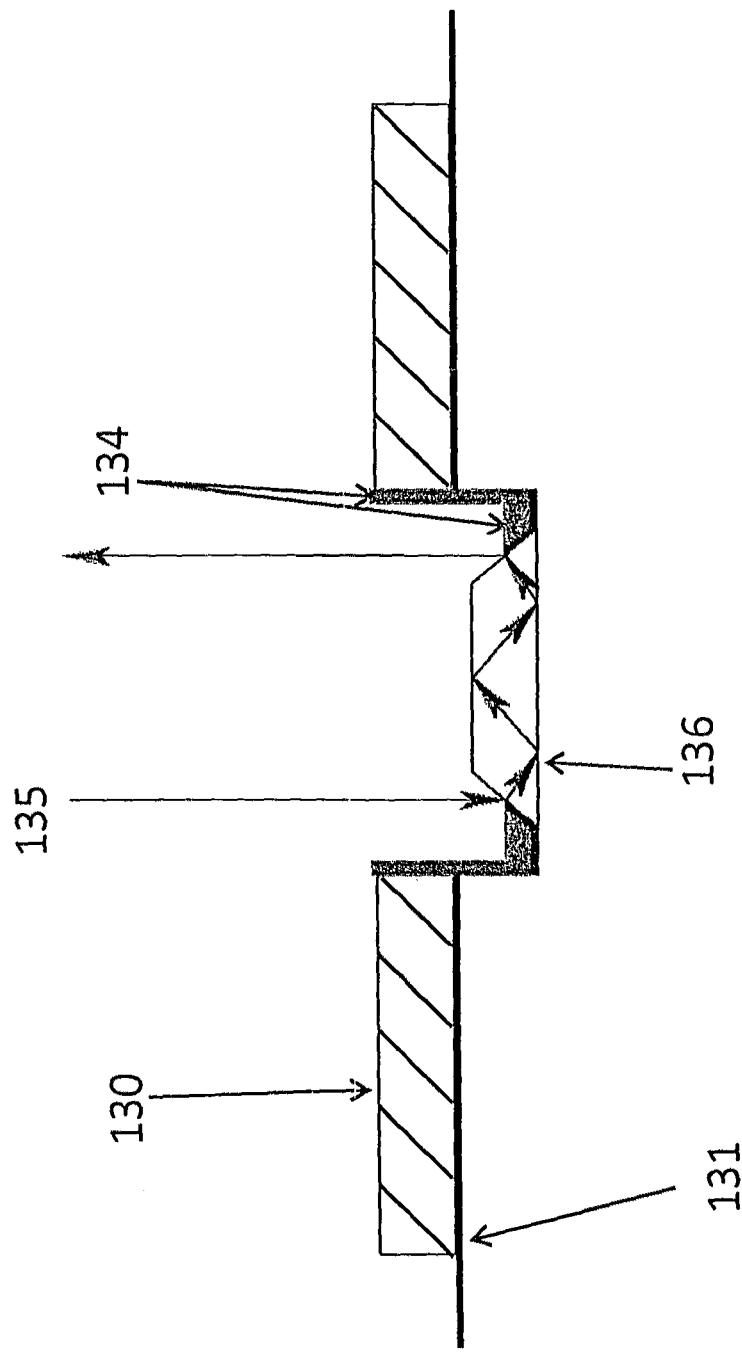

FIG. 14 depicts a cross-sectional view of another composite optical assembly. In particular here we show an ATR (attenuated total reflection) spectroscopic device. G. Müller, K. Abraham, and M. Schaldach, "*Quantitative ATR spectroscopy: some basic considerations,*" *Appl. Opt.* 20, 1182-1190 (1981). In this cross-sectional view, 131 is the liner or film of the single-use bioreactor, 130 is the LDPE or other compatible material, 134 is another, suitable polymeric material that is adhesively affixed to the LDPE. Component 136 is typically a high refractive optical index material (e.g.: $Al_2O_3$ or $YVO_4$, or high index glass, polycarbonate, or similar material). The high index is required to allow the frustrated total internal reflection. The incoming light is shown here as 135, and the evanescent sites or "bounce sites" are shown as 136. The exact optical refractive index and the number of bounce sites are determined by the sensitivity required by the absorption coefficient of the analyte in question at the wavelength used and other factors all of which are well known to the skilled artworker.

Figure 15:
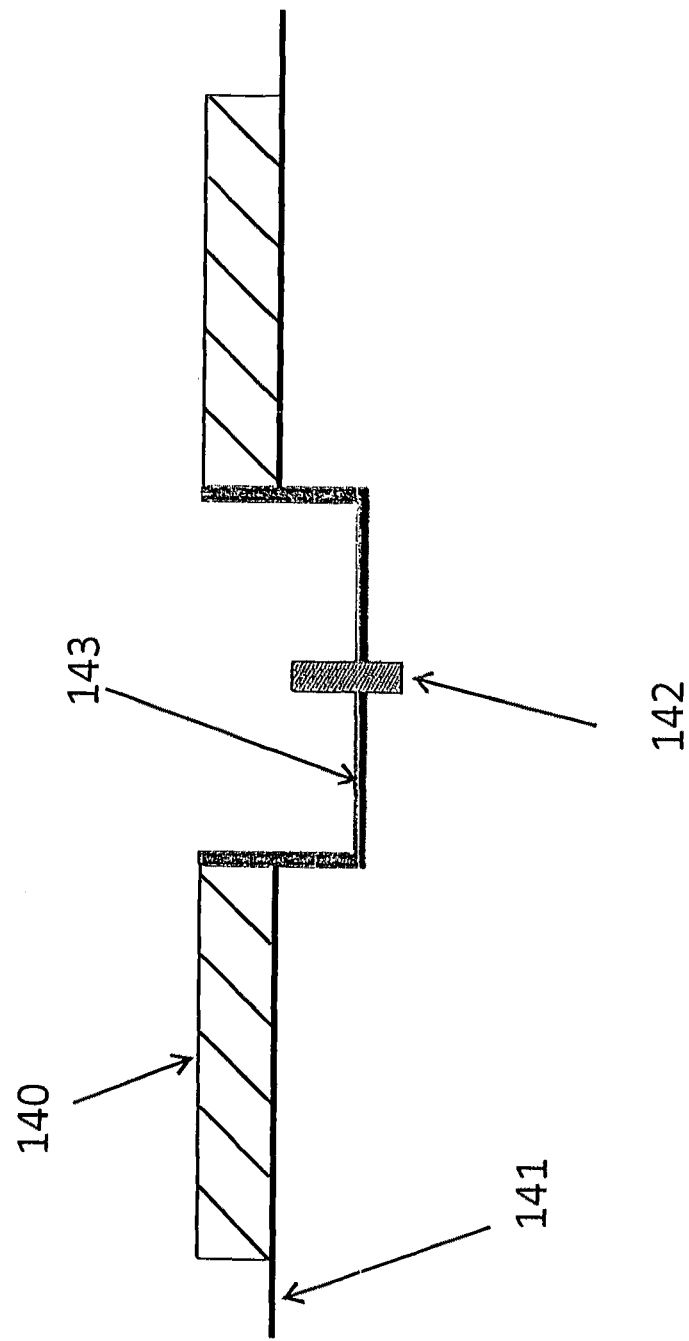

FIG. 15 depicts a cross-sectional view of a sensor assembly including an electrical device, 142, (e.g.: an ISFET) that is in contact with the contents of the bioreactor to provide a reading where 141 is the single-use bioreactor film and 140 is the composite's first bioreactor compatible material (e.g.: LDPE). The composite assembly's second compatible material 143 is adhesively affixed to 140. The electrical element, 142, can be molded directly into 143, adhesively affixed, or retained in place using a mechanical seal such as a compression fit using an o-ring or similar technique depending on the device and its particular properties. Note that such an electrical device could also utilize a chemically reactive material coating as the transduction mechanism, or comprise a microfluidic network superimposed on the electrical sensors.

Figure 16:
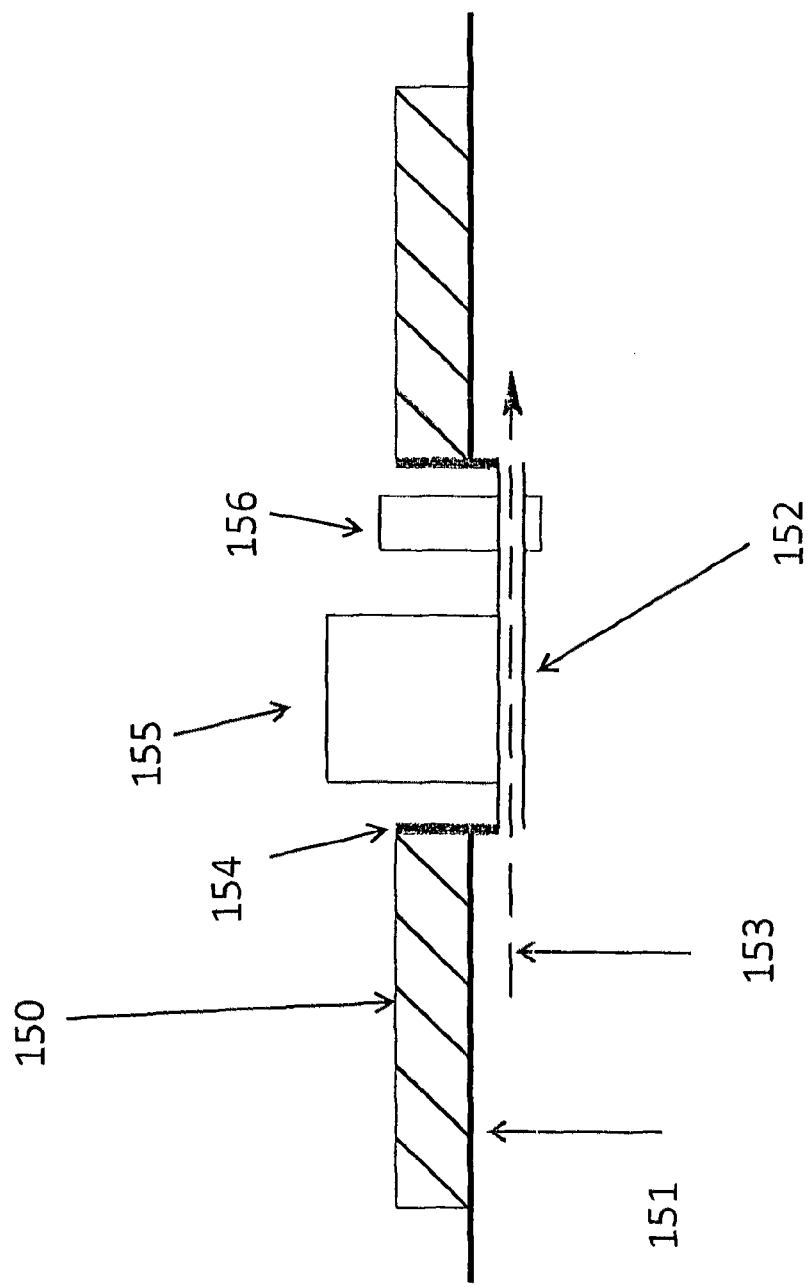
Figure 17:
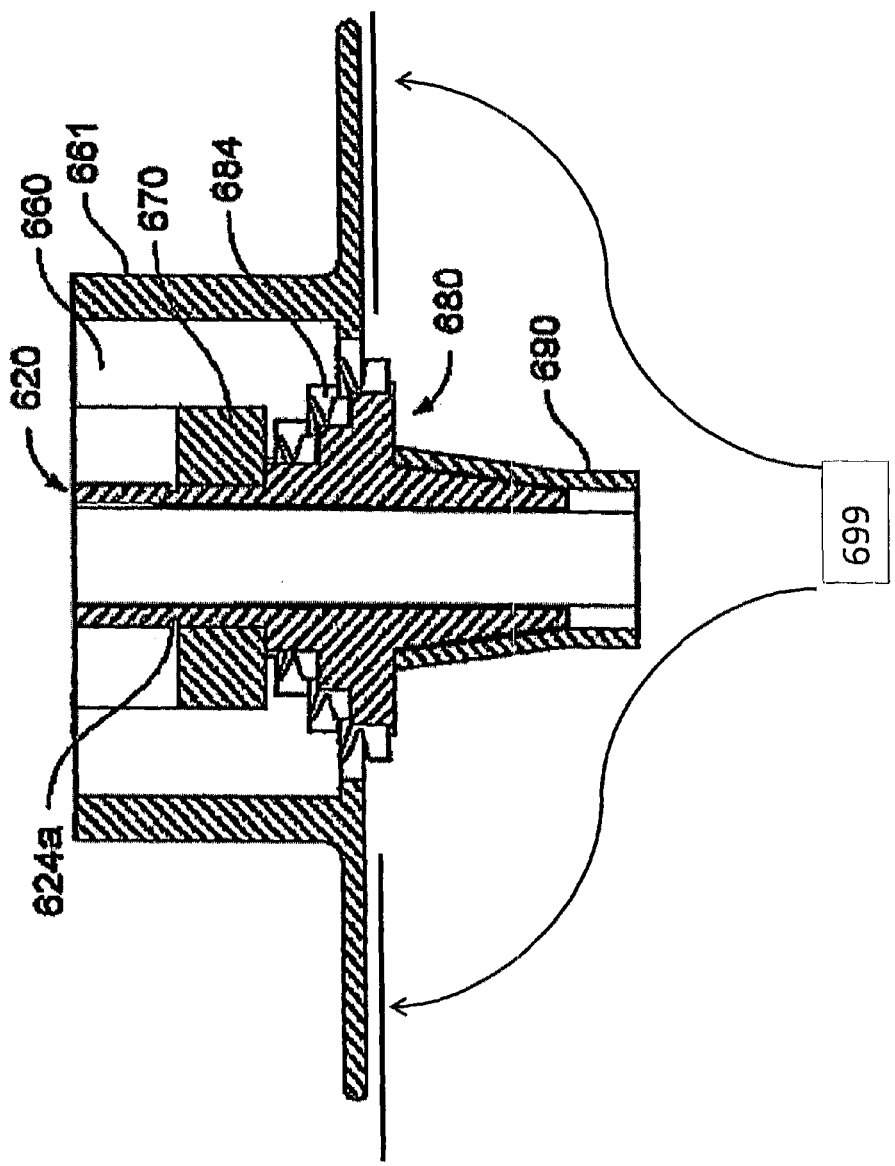

FIG. 16 shows a cross-sectional view of another type of composite sensor assembly where 151 is the single-use vessel film, and 150 is the composite assembly's film compatible material such as LDPE. The composite's second compatible material is shown as 154 and is adhesively affixed to 150. Item 155 represents an optical unit comprised of a light source and a detection system which may utilize a spectrometer or a set of filters to identify the spectral components of the returned light. The optical source will impinge upon 152 which is a generally tubular and is at least partially transparent to the light source. Element 152 is constructed so that the contents of the bioreactor can be continuously circulated through it allowing accurate, non-invasive, in-situ examination of the bioreactor contents. Circulation can, if desired, be facilitated by a pump, 156. The system shown can also be used to perform near-infrared absorption spectroscopic measurements, or Raman measurements of the bioreactor contents Earlier the suitability and advantages of fabricating composite mechanical assemblies for polymeric bioreactor vessels utilizing the bonding procedures of the present invention was indicated. This is because many of the liner style single-use bioreactors (and mixers) rely on a motor driven agitator to mix and help aerate the contents of the vessel. The agitator shaft must be introduced into the bioreactor vessel through a port which also constrains the shaft. A similar fundamental limitation imposed by material compatibility is encountered here as well. In FIG. 17 an agitation drive unit as described in of U.S. Pat. No. 7,384,783 (the teaching of which is incorporated herein by this reference) is shown. In FIG. 17, as per FIG. 6 of the aforementioned Patent, is shown a partial cross-section view of a rotational assembly 601, where the rotational assembly includes a bearing assembly 670 disposed between a hub 620 and an inner casing 660. Additionally, shown is a lower race bearing or the assembly 670 is in a fixed relation with the inner casing 660. Hub 620 can rotate relative to the race bearing and may include a guide 624a for receiving snap rings or retaining rings which can help maintain hub 620 in place. As shown, the outer casing 661 must be bonded to the single-use vessel wall 699. This requires that the casing 661 be constructed of a material compatible with the bioreactor vessel film, or casing 661 must be over-molded with a film compatible material (i.e., bondable to the film). Requiring material compatibility limits the selection of materials to materials similar to LDPE which then limits the ability to select casing materials with the optimal characteristics for the application (e.g.: tensile strength, elasticity, hardness etc.). Over-molding also limits the materials that can be used. Although ultra low density polyethylene used for the films can be sometimes be over-molded onto more rigid high density polyethylene (HDPE) even HDPE is generally sub-optimal for this application.

As described here, with the proper surface treatment many more suitable materials can be used for the mechanical unit (e.g.: the hub 620, and/or the bearing assembly 670) and be adhesively affixed to the outer casing 661. This provides an alternative and preferred path in accordance with the present invention to constructing the agitator drive assembly in a similar fashion to the sensor unit and port as previously described.

Additional mechanisms for bioprocessing applications that can benefit from the ability to utilize fundamentally different materials include but are not limited to spargers (aeration devices) and sampling ports. Single use bioreactors employ complex fits or membranes to provide the porous apertures required to convert gas flow into bubbles of certain sizes for gas mass transfer purposes and their design can be limited by the material selection and compatibility issue that affects sensors. Ports for autosamplers can also require multiple materials, as the materials that touch the bioprocess fluids sometimes need to be UV transparent in order to be sterilized in-situ. This is currently impossible using LDPE and similar materials as they absorb strongly in this region.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims.

We claim:

1. A composite sensor assembly for use with a polymeric bioprocess vessel, said sensor assembly comprising:
   i) a port comprising a high surface tension thermoplastic having a hollow portion and a base plate portion, at least said base plate portion comprising a polymer fusibly sealable to the bioprocess vessel at a hole in the wall thereof; and
   ii) a polymeric monitoring sensor unit including at least one electrical, and/or chemical and/or optical measurement component, said sensor unit including a base portion and being generally dish shaped and sized to fit inside the bore of the hollow portion of said port, and being adhesively retained therein, said port providing the monitoring sensor unit measurement component or components with access to the contents of said bioreactor vessel, which component or components include means for providing incoming optical and/or electrical signals and means for collecting and transmitting measurement signals emitted by the components.

2. A sensor assembly in accordance with claim 1 wherein said polymeric monitoring sensor unit includes a plurality of electrical, and/or chemical and/or optical measurement components.

3. A sensor assembly in accordance with claim 1 wherein said monitoring sensor unit has a peripheral rim extending above the base thereof.

4. A sensor assembly in accordance with claim 3 wherein said sensor unit has cup shaped depressions in the inner surface of the base thereof.

5. A sensor assembly in accordance with claim 1 wherein the sensor unit has a generally circular shape.

6. A sensor unit in accordance with claim 2 wherein each of said measurement components is situated in a separate cup shaped depression in the base of said sensor unit and wherein each said cup shaped depression includes a surrounding rim which extends above the inner surface of the sensor unit base.

7. A sensor unit in accordance with claim 6 wherein at least one of said cup shaped depressions has a light shield positioned over the top thereof.

8. A sensor unit in accordance with claim 1 wherein said sensor unit comprises a polymer selected from the group consisting of polycarbonates, co-polyesters, cycloolefin copolymers, poly-olefins, and polystyrene.

9. A sensor assembly in accordance with claim 1 wherein a USP Class VI adhesive is present between said sensor unit and said port.

10. A sensor assembly in accordance with claim 9 wherein said adhesive is selected from the group consisting of one or two part epoxy resins, UV cured epoxies, cyanoacrylates, platinum cured silicones and polyurethanes.

11. A sensor assembly in accordance with claim 1 wherein said high surface tension thermoplastic is low or ultra low density polyethylene or ethylene vinyl acetate copolymer.

12. A sensor assembly in accordance with claim 1 wherein said monitoring sensor unit is of substantially tubular configuration.

13. A sensor assembly in accordance with claim 12 wherein said monitoring sensor unit comprises a substantially opaque sheath.

14. A sensor assembly in accordance with claim 12 wherein said measurement component comprises a fluorescent sensor spot.

15. A sensor assembly in accordance with claim 14 wherein said sensor unit comprises a light shield.

16. A sensor assembly in accordance with claim 1 wherein said sensor unit comprises a free space optical density measurement component.

17. A sensor assembly in accordance with claim 1 wherein said sensor unit comprises an optical spectroscopy measurement component.

18. A sensor assembly in accordance with claim 1 wherein said sensor unit comprises an ISFET unit.

19. A process for the fabrication of the sensor assembly of claim 1 wherein said sensor unit is adhesively retained by interposing between either or both of an inner surface of the hollow portion of said port and an outer surface of said sensor unit an adhesive selected from the group consisting of one or two part epoxy resins, UV curable epoxies, cyanoacrylates, silicones and polyurethanes.

* * * * *